(12) United States Patent
Raulerson et al.

(10) Patent No.: US 10,471,552 B2
(45) Date of Patent: Nov. 12, 2019

(54) SYSTEMS AND METHODS FOR THERMAL LOCATION OF COOLING HOLES

(71) Applicant: United Technologies Corporation, Hartford, CT (US)

(72) Inventors: David A. Raulerson, Palm Beach Garden, FL (US); Kevin D. Smith, Glastonbury, CT (US); Zhong Ouyang, Glastonbury, CT (US); Lisa J. Brasche, Ellington, CT (US); William J. Brindley, Hebron, CT (US); David N. Potter, East Hampton, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 285 days.

(21) Appl. No.: 15/030,326

(22) PCT Filed: Jan. 13, 2015

(86) PCT No.: PCT/US2015/011176
§ 371 (c)(1),
(2) Date: Apr. 18, 2016

(87) PCT Pub. No.: WO2015/108858
PCT Pub. Date: Jul. 23, 2015

(65) Prior Publication Data
US 2016/0318135 A1  Nov. 3, 2016

Related U.S. Application Data

(60) Provisional application No. 61/928,327, filed on Jan. 16, 2014.

(51) Int. Cl.
*B23P 6/00* (2006.01)
*F01D 9/02* (2006.01)
*F01D 25/12* (2006.01)

(52) U.S. Cl.
CPC ............. *B23P 6/002* (2013.01); *F01D 9/02* (2013.01); *F01D 25/12* (2013.01);
(Continued)

(58) Field of Classification Search
CPC .. F01D 5/005; F05D 2230/72; F05D 2230/80; F05B 2230/80; F05B 2230/90;
(Continued)

(56) References Cited

U.S. PATENT DOCUMENTS 6,380,512 B1    4/2002  Emer
6,420,677 B1 *  7/2002  Emer .................. B23K 26/40
                                                  219/121.71
(Continued)

FOREIGN PATENT DOCUMENTS

EP    1941965    7/2008
EP    2466069    6/2012

OTHER PUBLICATIONS

International Search Report and Written Opinion dated Apr. 6, 2015 in Application No. PCT/US2015/011176.
(Continued)

*Primary Examiner* — Jason L Vaughan
*Assistant Examiner* — Amanda Kreiling
(74) *Attorney, Agent, or Firm* — Snell & Wilmer, L.L.P.

(57) ABSTRACT

Systems and methods are disclosed herein for repairing components. A material layer may be deposited on a surface of a component. The material layer may cover a cooling hole. A pulsed heat source may heat the component and the material layer. An infrared camera may take a series of images of the component. A location of the cooling hole may be identified based on thermal properties of the component. A removal tool may remove a portion of the material layer in order to expose the cooling hole.

11 Claims, 7 Drawing Sheets

(52) U.S. Cl.
CPC ...... *B23P 2700/06* (2013.01); *F05D 2220/32* (2013.01); *F05D 2230/13* (2013.01); *F05D 2230/80* (2013.01); *F05D 2260/81* (2013.01); *F05D 2300/611* (2013.01)

(58) Field of Classification Search
CPC ......... Y10T 29/49732; Y10T 29/49742; Y10T 29/49734
See application file for complete search history.

(56) References Cited

U.S. PATENT DOCUMENTS

| | | | | |
|---|---|---|---|---|
| 6,723,951 B1* | 4/2004 | McGraw | ................ | B23K 26/04 219/121.71 |
| 6,847,004 B2 | 1/2005 | Das et al. | | |
| 8,577,120 B1* | 11/2013 | Koshti | ................. | G06T 7/0004 250/341.8 |
| 8,810,644 B2* | 8/2014 | Bunker | ................... | F01D 5/005 348/86 |
| 2002/0076097 A1* | 6/2002 | Vaidyanathan | ......... | B23P 6/002 382/154 |
| 2002/0172410 A1* | 11/2002 | Shepard | ................ | G01N 25/72 382/141 |
| 2006/0291716 A1 | 12/2006 | Vaidyanathan | | |
| 2009/0270014 A1 | 10/2009 | Miller | | |
| 2013/0020292 A1* | 1/2013 | Elfizy | ................. | B23K 26/389 219/121.71 |
| 2013/0268107 A1* | 10/2013 | Bostanjoglo | ............ | F01D 5/005 700/166 |

OTHER PUBLICATIONS

International Preliminary Report on Patentability dated Jul. 19, 2016 in Application No. PCT/US2015/011176.
EP Search Report dated Aug. 14, 2017 in EP Application No. 15737252.5.

* cited by examiner

SYSTEMS AND METHODS FOR THERMAL LOCATION OF COOLING HOLES

CROSS-REFERENCE TO RELETED APPLICATIONS

This application is U.S. national phase filing under 35 U.S.C. § 371 of PCT/US2015/011176 filed on Jan. 13, 2015 and entitle "SYSTEMS AND METHODS FOR THERMAL LOCATION OF COOLING HOLES," which claims priority from U.S. Provisional Application No. 61/928,327 filed on Jan. 16, 2014 and entitled "SYSTEM AND METHODS FOR THERMAL LOCATION OF COOLING HOLES." Both of the aforementioned applications are incorporated herein by reference in their entirety.

FIELD

The present disclosure relates generally gas turbine engines. More particularly, the present disclosure relates to systems and methods for thermal location of cooling holes in components in gas turbine engines.

BACKGROUND

Gas turbine engines typically comprise components which include cooling holes. During repair of the components, a worn or distressed material layer (e.g., a thermal barrier coating) may be removed and a replacement layer may be applied to the component. The replacement layer may cover the prior cooling holes and obscure the cooling holes from view. It may be desirable to nondestructively locate the cooling holes in order to remove the material covering the cooling holes.

SUMMARY

A method of repairing a component may comprise depositing a material layer on a surface of the component. The component may be heated with a pulsed heat source. Thermal properties of the component may be measured. A cavity in the component may be located based on the thermal properties. A portion of the material layer may be removed to expose the cavity.

The material layer may comprise a thermal barrier layer. Measuring the thermal properties may comprise capturing a series of infrared images of the component. The cavity may comprise a cooling hole. Locating the cavity may comprise locating a center of the cavity. The removing the portion of the material layer may comprise aligning a laser drill with an angle of the cavity. The component may comprise an aircraft component. The method may further comprise creating a 2-dimensional thermal image of the component. The method may further comprise comparing the cavity to known specifications of the component in order to determine an angle of the cavity relative to the surface of the component. The method may further comprise setting a power of a laser drill such that the removing the portion of the material layer removes a portion of the material layer without damaging the component.

A method of locating a cooling hole may comprise heating a component and a material layer disposed on a surface of the component with a pulsed heat source. A series of thermal images of the component may be captured with an infrared camera. The series of thermal images may be processed to identify temperature gradients on the component. Based on the temperature gradients, a location of a center of a first cooling hole may be identified.

In various embodiments, the method may further comprise comparing the location of the center of the first cooling hole with known specifications for the component. The method may further comprise identifying an angle of the first cooling hole relative to the surface of the component based on the known specifications. The method may further comprise heating the component with the pulsed heat source a second time. The method may further comprise locating a center of a second cooling hole.

A system for repairing a component may comprise a pulsed heat source configured to heat the component. The system may comprise an infrared camera configured to capture a series of thermal images of the component. The system may comprise a computer coupled to the infrared camera and configured to identify a location of a cooling hole. The system may comprise a removal tool configured to remove a portion of a material layer covering the cooling hole.

The removal tool may comprise a laser drill coaxial with the infrared camera. The computer may comprise stored specifications of the component. The computer may be configured to align the removal tool with an angle of the cooling hole based on the stored specifications. The computer may be configured to direct movement of the removal tool.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

Conventional systems for thermally locating cooling holes may include heating a component and thermally imaging the component in order to detect thermal variations on the surface. However, heating the entire component may take long durations and use large amounts of energy. Additionally, some components may be too large or otherwise unsuited to such methods.

Systems and methods are disclosed herein for thermally locating cooling holes. Although described primarily with reference to a turbine vane, the disclosed systems and methods may be applied to any component comprising cooling holes which are obscured from view. Similarly, although described primarily with respect to cooling holes, the disclosed systems and methods may be used to detect the location of many subsurface features of a component.

During repair of a turbine vane, a material layer, such as a thermal barrier coating ("TBC") may be applied to the surface of the turbine vane. The TBC may cover cooling holes in the turbine vane. A pulsed heat source may heat the surface of the turbine vane and the TBC. An infrared camera may map thermal patterns, or thermograms, of the turbine vane surface over time. Variations in the thermograms may indicate the location of the cooling holes. A removal tool, such as a laser drill, may be directed at the location of the cooling holes and may remove the TBC covering the cooling holes.

Figure 1:
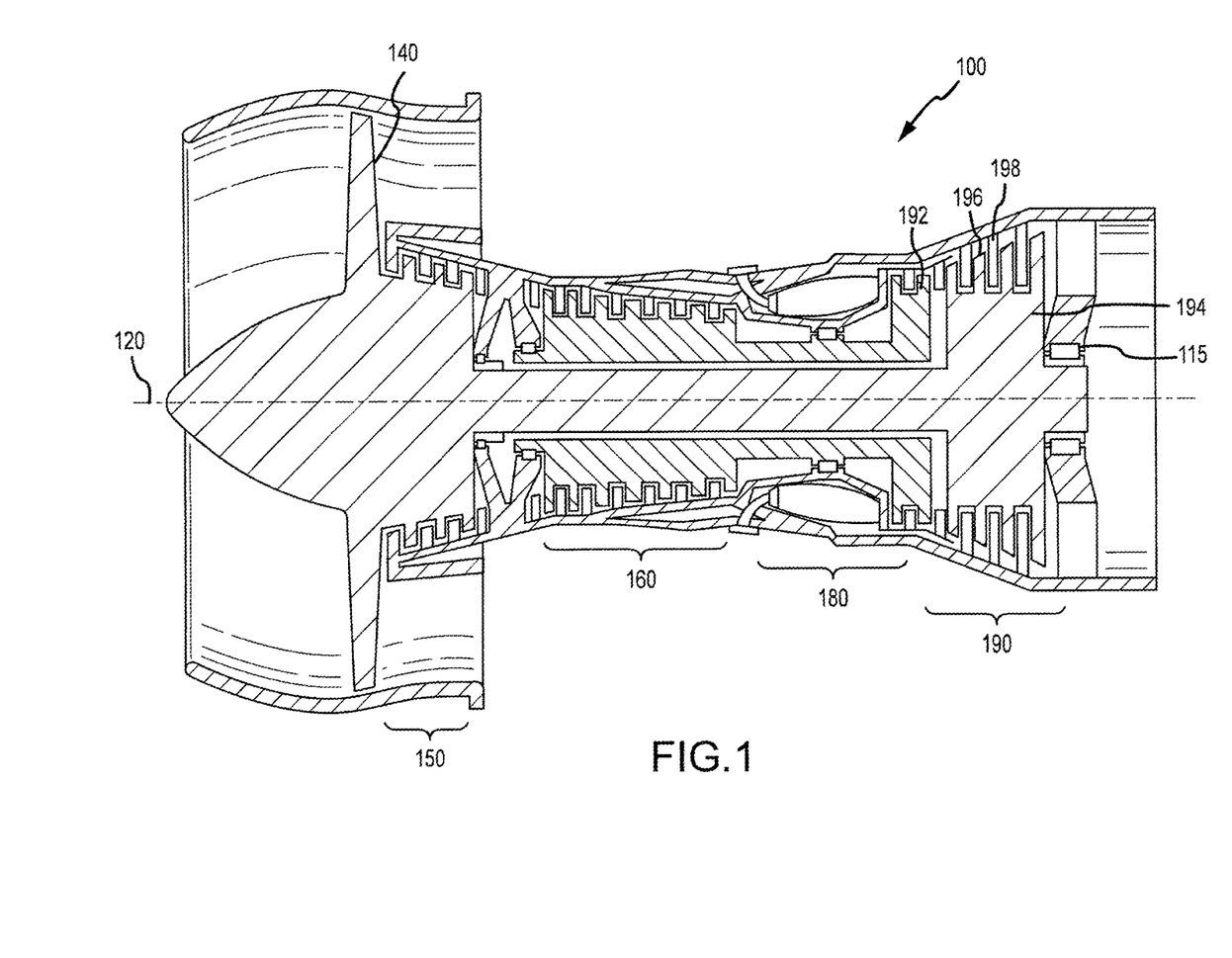
FIG. 1 illustrates a schematic cross-section view of a gas turbine engine in accordance with various embodiments.

Referring to FIG. 1, a gas turbine engine 100 (such as a turbofan gas turbine engine) is illustrated according to various embodiments. Gas turbine engine 100 is disposed about axial centerline axis 120, which may also be referred to as axis of rotation 120. Gas turbine engine 100 may comprise a fan 140, compressor sections 150 and 160, a combustion section 180, and a turbine section 190. Air compressed in the compressor sections 150, 160 may be mixed with fuel and burned in combustion section 180 and expanded across turbine section 190. Turbine section 190 may include high pressure rotors 192 and low pressure rotors 194, which rotate in response to the expansion. Turbine section 190 may comprise alternating rows of rotary airfoils or blades 196 and static airfoils or vanes 198. A plurality of bearings 115 may support spools in the gas turbine engine 100. Many of the components of gas turbine engine 100 may comprise cooling holes. FIG. 1 provides a general understanding of the sections in a gas turbine engine, and is not intended to limit the disclosure. The present disclosure may extend to all types of turbine engines, including turbofan gas turbine engines and turbojet engines, for all types of applications.

The forward-aft positions of gas turbine engine 100 lie along axis of rotation 120. For example, fan 140 may be referred to as forward of turbine section 190 and turbine section 190 may be referred to as aft of fan 140. Typically, during operation of gas turbine engine 100, air flows from forward to aft, for example, from fan 140 to turbine section 190. As air flows from fan 140 to the more aft components of gas turbine engine 100, axis of rotation 120 may also generally define the direction of the air stream flow.

Figure 2:
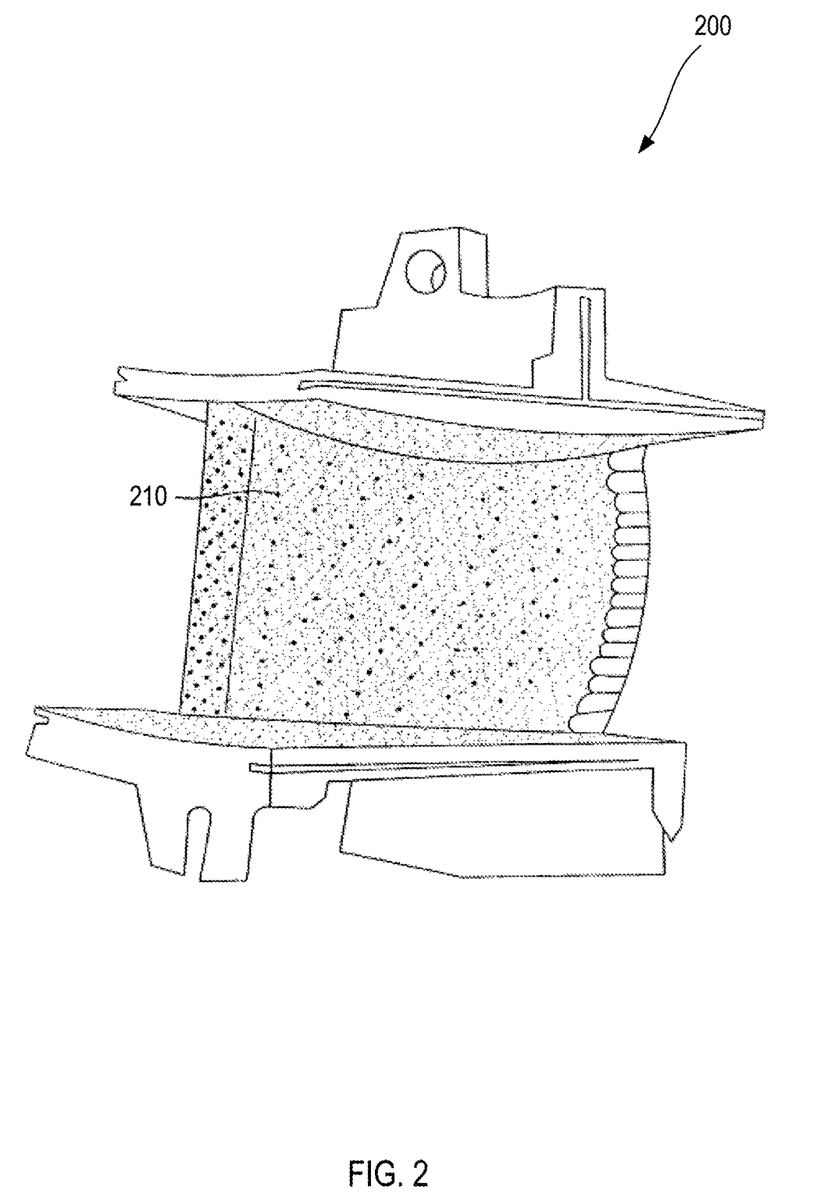
FIG. 2 illustrates a perspective view of a turbine vane in accordance with various embodiments.

Referring to FIG. 2, turbine vane 200 is illustrated according to various embodiments. Turbine vane 200 may comprise a plurality of cooling holes 210. During repair of turbine vane 200, a material layer (not shown), such as a TBC, may be placed on turbine vane 200. The TBC may obstruct cooling holes 210 from view.

Figure 3:
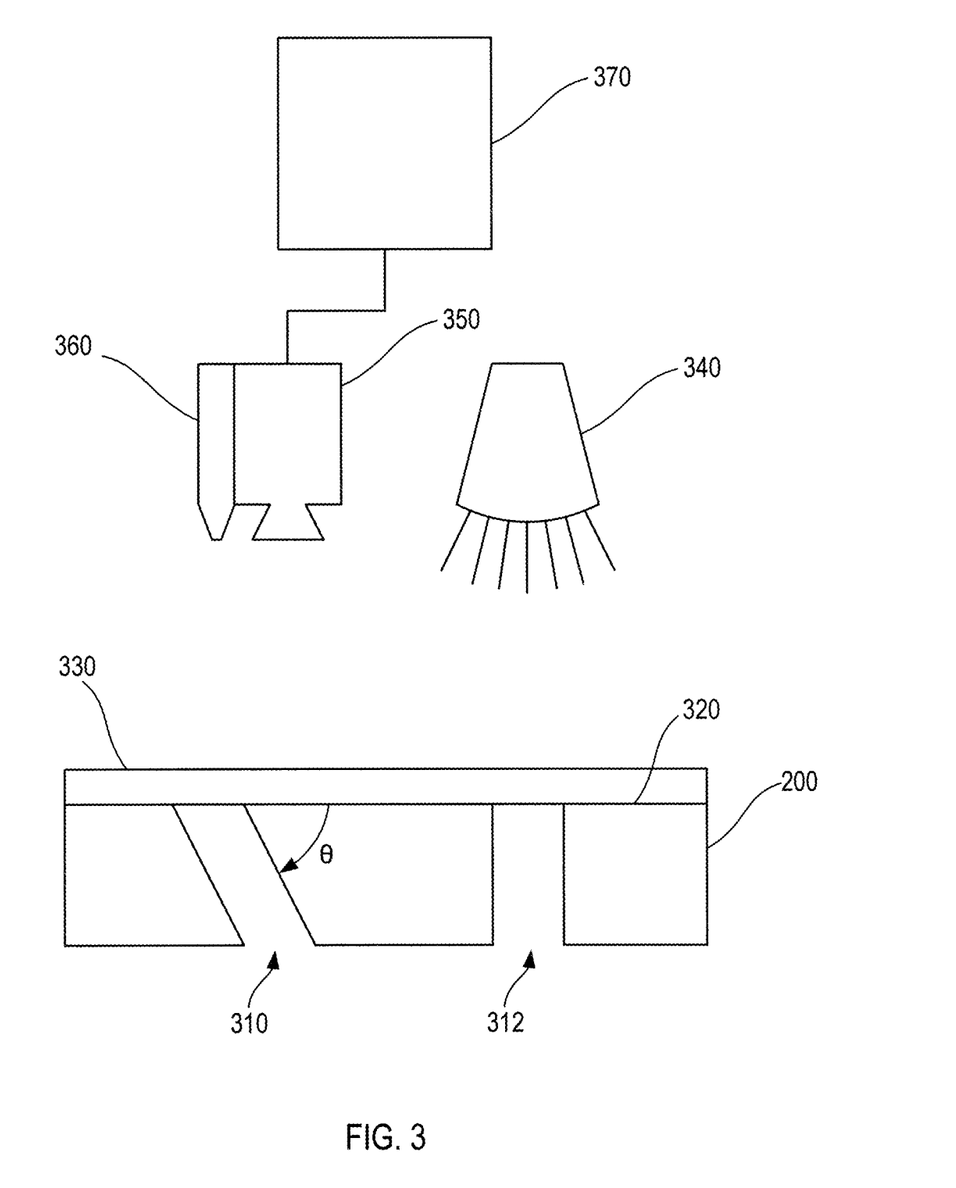
FIG. 3 illustrates a cross-section view of a turbine vane in accordance with various embodiments.

Referring to FIG. 3, a cross-section of a portion of turbine vane 200 is illustrated according to various embodiments. Turbine vane 200 may comprise a first cooling hole 310 and a second cooling hole 312. The various cooling holes may be positioned at various angles relative to an outer surface 320 of turbine vane 200. For example, first cooling hole 310 may be positioned at an angle θ relative to outer surface 320. As shown, angle θ is 60°. In various embodiments, second cooling hole 312 may be substantially perpendicular to outer surface 320. However, cooling holes may be positioned at any angle relative to outer surface 320.

A material layer 330 may be placed on outer surface 320 during repair of turbine vane 200. Material layer 330 may cover first cooling hole 310 and second cooling hole 312. However, it may be desirable to remove portions of material layer 330 in order to expose first cooling hole 310 and second cooling hole 312.

A pulsed heat source 340 may be directed at outer surface 320. In pulsed thermography, a brief pulse of light may be used to heat turbine vane 200 and material layer 330. Pulsed heat source 340 may comprise any heat source suitable for performing pulsed thermography. In various embodiments, pulsed heat source 340 may comprise a xenon flash lamp array, a quartz flash source and/or an LED flash source. Pulsed heat source 340 may emit light pulses for durations such as between 20 milliseconds and 30 milliseconds, or between 1 millisecond and 40 milliseconds. Turbine vane 200 may heat and cool non-uniformly due to subsurface variations, such as first cooling hole 310 and second cooling hole 312.

An infrared camera 350 may thermally image turbine vane 200. Infrared camera 350 may comprise any suitable infrared camera known in the art. Such cameras may have a frame with an area defined by a finite number of pixels. Infrared camera 350 may detect changes in surface temperature as turbine vane 200 heats during the light pulse and subsequently cools. Each pixel of infrared camera 350 may record thermal data from a specific location of turbine vane 200. Thus, a single pixel may provide data of the thermal characteristics of a specific location as turbine vane 200 heats and cools.

In various embodiments, a removal tool 360 may be configured to remove portions of material layer 330. In various embodiments, removal tool 360 may comprise a laser drill configured to remove portions of material layer 330. However, in various embodiments, removal tool 360 may comprise at least one of a water jet, mechanical drill, pencil grit blast, or any other device capable of removing a portion of material layer 330. In various embodiments, removal tool 360 may be coupled to and/or coaxial with infrared camera 350. Thus, in response to infrared camera 350 centering on a specific location, such as first cooling hole 310, removal tool 360 may be focused on the specific location.

In various embodiments, at least one of infrared camera 350 and removal tool 360 may be coupled to a computer 370. Computer 370 may be configured to process data measured by infrared camera 350. Computer 370 may further be configured to direct movement of infrared camera 350 and/or removal tool 360.

Figure 4:
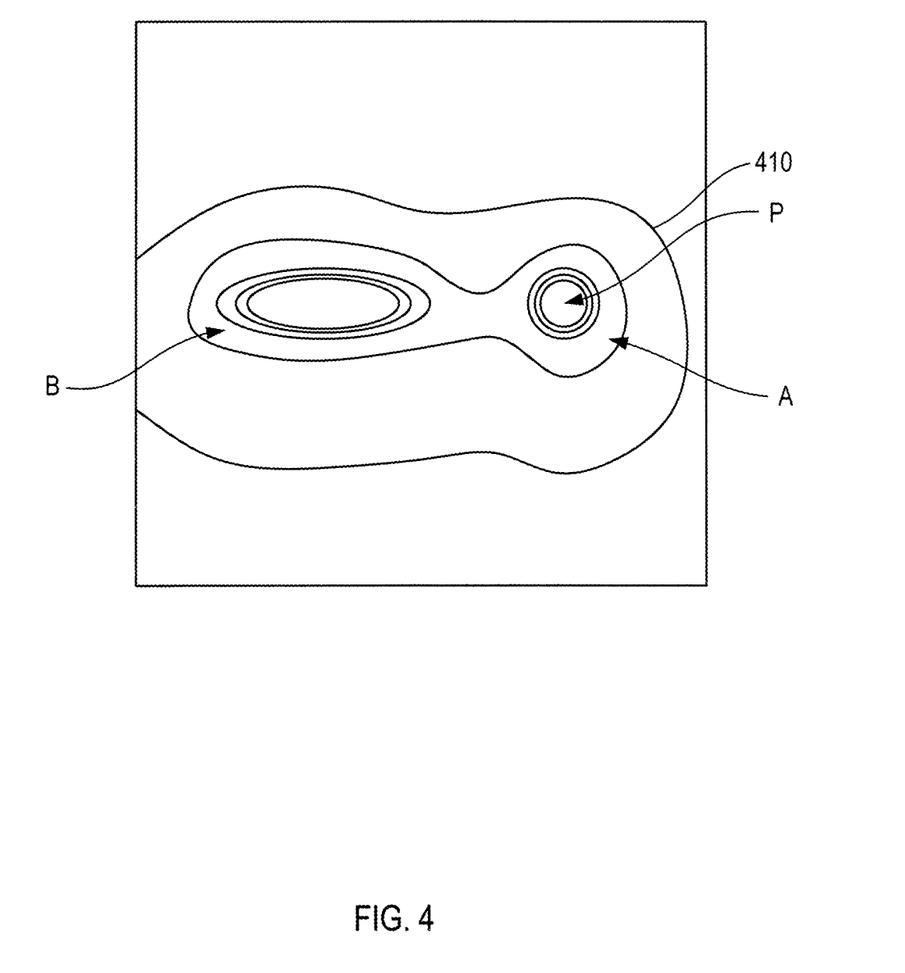
FIG. 4 illustrates a 2-dimensional thermal image in accordance with various embodiments.

Referring to FIG. 4, a 2-dimensional thermal image may be constructed based on data from the individual pixels of infrared camera 350. Isotherms 410 may connect locations of substantially similar temperatures or thermal conductivity. Areas with few isotherms may represent areas of relatively little variation in thermal conductivity, and areas with isotherms spaced closely together may represent relatively large gradients in thermal conductivity.

In region A, isotherms 410 may be substantially circular, and may thus represent a cooling hole which is substantially perpendicular to outer surface 320, such as first cooling hole 310 shown in FIG. 3. A center point P of isotherms 410 in region A may indicate a location of the center of second cooling hole 312. In region B, isotherms 410 may be elongated or ovoid. Thus, isotherms 410 in region B may represent a cooling hole which is located at an angle relative to outer surface 320, such as first cooling hole 310 shown in FIG. 3.

An angle of first cooling hole 310 may be determined by various methods. In various embodiments, a location of first cooling hole 310 may be compared to known specifications for turbine vane 200. The specifications may be stored in computer 370. The specifications may comprise the known angle for cooling holes at the location being thermally imaged. The known angle may be used to align removal tool 360 with the cooling hole.

Figure 5:
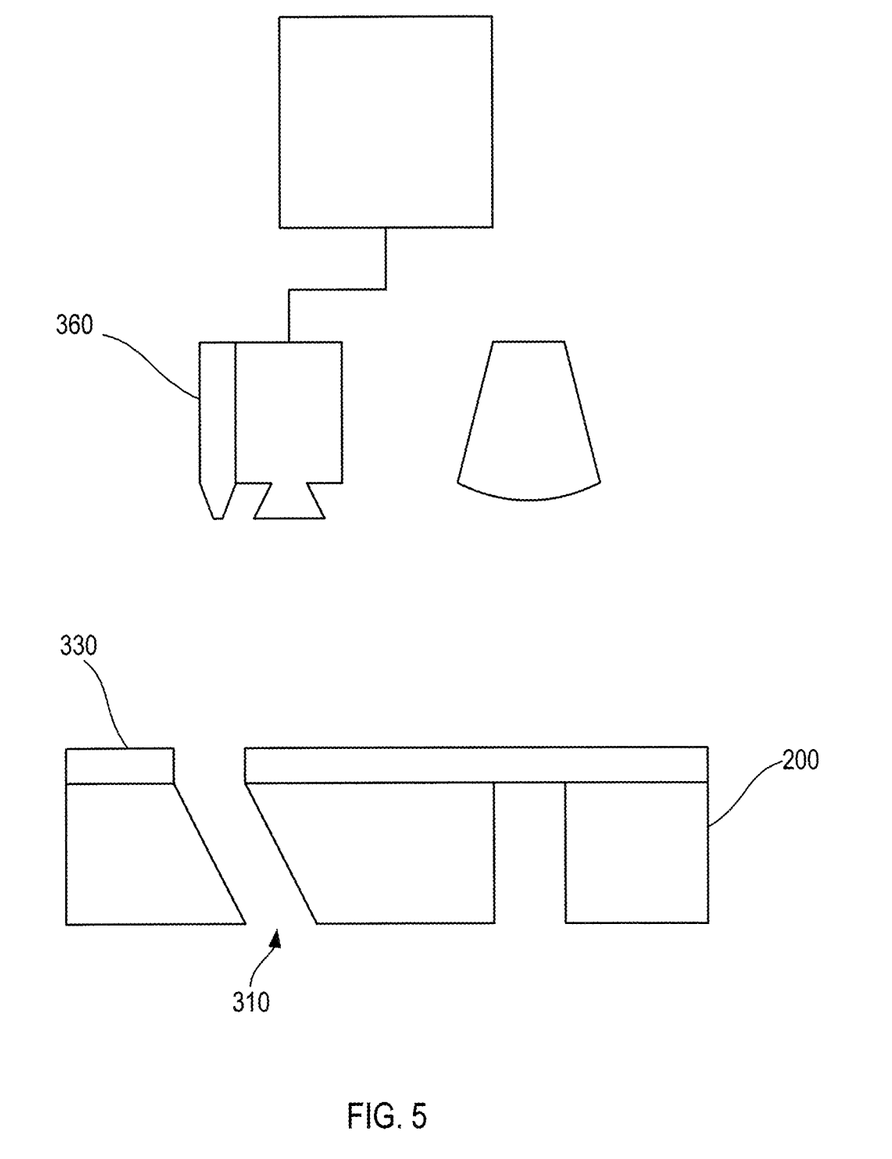
FIG. 5 illustrates a cross-section view of a turbine vane with a portion of a material layer removed in accordance with various embodiments.

Referring to FIG. 5, turbine vane 200 is illustrated with a portion of material layer 330 removed. In various embodiments, a power of removal tool 360 may be set such that removal tool 360 may remove material layer 330 without damaging turbine vane 200. Removal tool 360 may be focused on a center of first cooling hole 310 and may remove a portion of material layer 330 which covers first cooling hole 310. The power level of removal tool 360 may prevent damage to turbine vane 200 even if the laser beam emitted from removal tool 360 contacts turbine vane 200.

Figure 6:
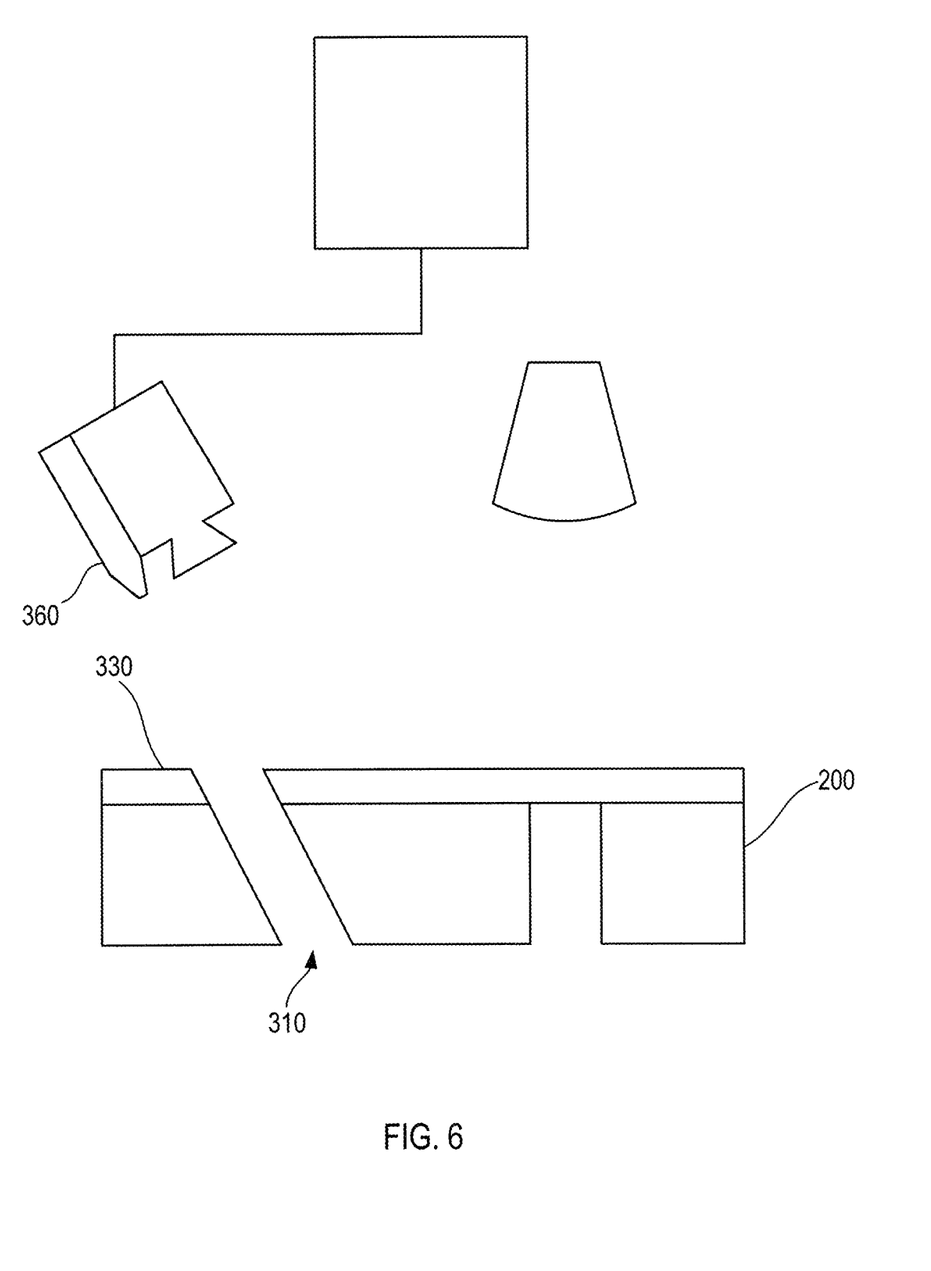
FIG. 6 illustrates a cross-section view of a turbine vane with an angled portion of a material layer removed in accordance with various embodiments.

Referring to FIG. 6, turbine vane 200 is illustrated with an angled portion of material layer 330 removed. In various embodiments, it may be desirable to angle removal tool 360 with the cooling holes in order to prevent damage to turbine vane 200 or to align the removed portion of material layer 330 with the cooling holes. Removal tool 360 may be positioned to align with first cooling hole 310, and removal tool 360 may remove the portion of material layer 330 covering first cooling hole 310. After removal tool 360 has removed the portion of material layer 330 covering first cooling hole 310, a laser beam emitted from removal tool 360 may pass through first cooling hole 310 without contacting turbine vane 200.

Figure 7:
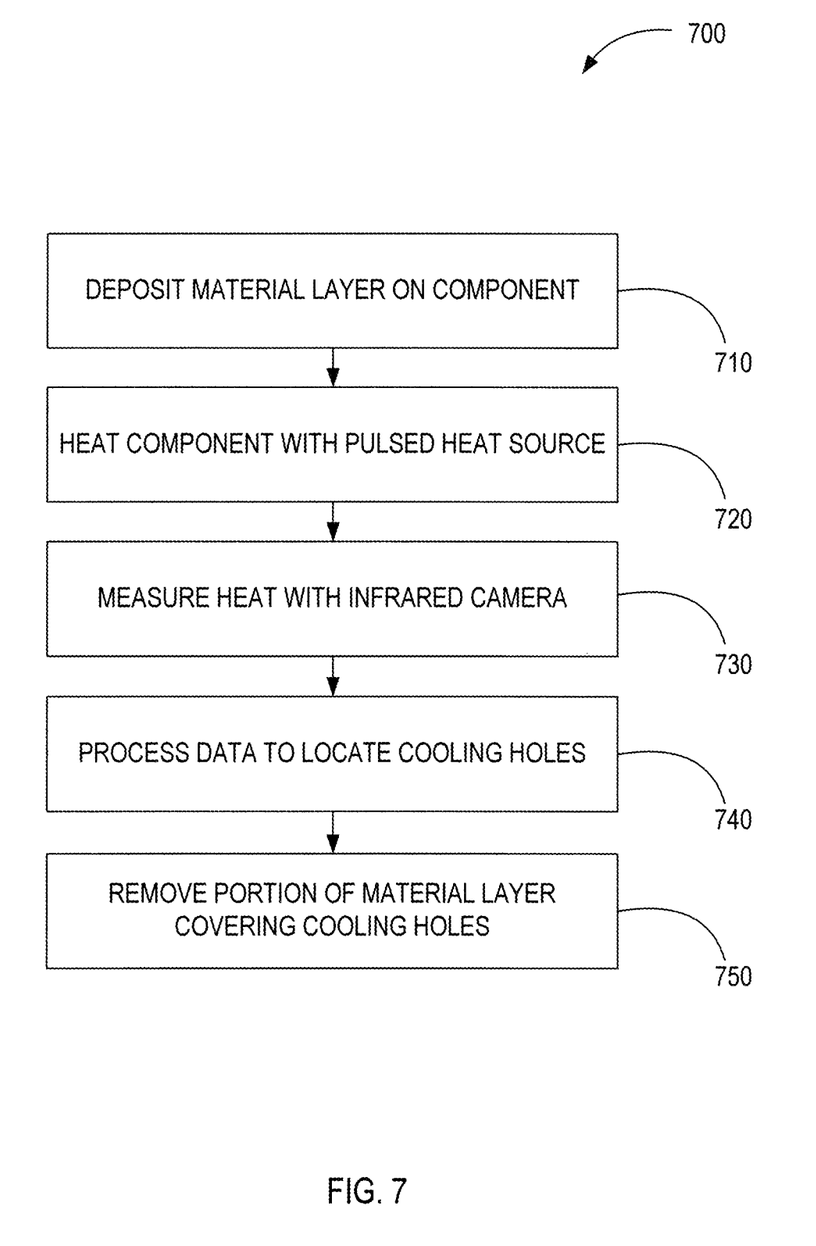
FIG. 7 illustrates a flow diagram of a process for repairing a component in accordance with various embodiments.

Referring to FIG. 7, a flowchart of a process for repairing a component with cooling holes is illustrated according to various embodiments. A material layer may be deposited on a surface of a component (step 710). In various embodiments, the material layer may comprise a thermal barrier coating. The material layer may cover a cavity, such as cooling holes in the component. A pulsed heat source may heat the component and the material layer (step 720). The component may heat and cool unevenly due to the presence of the cooling holes. An infrared camera may capture heat emitted by the component (step 730). In various embodiments, the infrared camera may capture a series of images over time as the component heats and subsequently cools. The data captured by the infrared camera may be processed to locate the cooling holes (step 740). A removal tool may remove the portion of the material layer covering a cooling hole (step 750). In various embodiments, the removal tool may be aligned with an angle of the cooling hole relative to the surface of the component. In various embodiments, the pulsed heat source may heat the component a second time, and a second cooling hole may be located. The removal tool may then remove the portion of the material layer covering the second cooling hole. The process may continue until the material layer has been removed from all desired cooling holes.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of repairing a component comprising:
depositing a material layer on a surface of the component;
heating the component using a pulsed heat source;
measuring, by an infrared camera, thermal properties of the component;
locating, by the infrared camera, a cavity in the component based on the thermal properties;
comparing the cavity with a known specification for the component;
identifying an angle of the cavity relative to the surface of the component based on the known specification;
centering a removal tool on the cavity at the angle in response to the infrared camera locating the cavity; and
removing, by the removal tool, a portion of the material layer to expose the cavity, wherein the heating of the component further comprises emitting light pulses for between 1 millisecond and 40 milliseconds.

2. The method of claim 1, wherein the material layer comprises a thermal barrier layer.

3. The method of claim 1, wherein the measuring the thermal properties comprises capturing a series of infrared images of the component.

4. The method of claim 1, wherein the cavity comprises a cooling hole.

5. The method of claim 1, wherein the locating the cavity comprises locating a center of the cavity.

6. The method of claim 1, wherein the component comprises an aircraft component.

7. The method of claim 1, further comprising creating a 2-dimensional thermal image of the component.

8. The method of claim 1, further comprising setting a power of a laser drill such that the removing the portion of the material layer removes a portion of the material layer without damaging the component.

9. The method of claim 1, wherein the removal tool is co-axial with the infrared camera.

10. A method of repairing a component comprising:
depositing a material layer on a surface of the component;
heating the component using a pulsed heat source, wherein the pulsed heat source is at least one of a xenon flash lamp array, a quartz flash source or an LED flash source;
measuring, by an infrared camera, thermal properties of the component;
locating, by the infrared camera, a cavity in the component based on the thermal properties;
comparing the cavity with a known specification for the component
identifying an angle of the cavity relative to the surface of the component based on the known specification;
centering a removal tool on the cavity at the angle in response to the infrared camera locating the cavity; and
removing, by the removal tool, a portion of the material layer to expose the cavity.

11. A method of repairing a component comprising:
depositing a material layer on a surface of the component;
heating the component using a pulsed heat source;
measuring, by an infrared camera, thermal properties of the component, wherein the measuring includes capturing a series of infrared images based on the pulsed heat source;
locating, by the infrared camera, a cavity in the component based on the thermal properties;
comparing the cavity with a known specification for the component;
identifying an angle of the cavity relative to the surface of the component based on the known specification;
centering a removal tool on the cavity at the angle in response to the infrared camera locating the cavity; and
removing, by the removal tool, a portion of the material layer to expose the cavity.

* * * * *